(12) United States Patent
Cohen (10) Patent No.: US 9,572,649 B2
(45) Date of Patent: Feb. 21, 2017

(54) IMPLANTABLE PROSTHESIS FOR REPAIRING OR REINFORCING AN ANATOMICAL DEFECT

(71) Applicant: Covidien LP, Mansfield, MA (US)

(72) Inventor: Matthew D. Cohen, Berlin, CT (US)

(73) Assignee: Covidien LP, Mansfield, MA (US)

( * ) Notice: Subject to any disclaimer, the term of this patent is extended or adjusted under 35 U.S.C. 154(b) by 47 days.

(21) Appl. No.: 14/345,830

(22) PCT Filed: Oct. 1, 2012

(86) PCT No.: PCT/US2012/058248
§ 371 (c)(1),
(2) Date: Mar. 19, 2014

(87) PCT Pub. No.: WO2013/049795
PCT Pub. Date: Apr. 4, 2013

(65) Prior Publication Data
US 2015/0209127 A1  Jul. 30, 2015

Related U.S. Application Data

(60) Provisional application No. 61/541,551, filed on Sep. 30, 2011.

(51) Int. Cl.
*A61F 2/02* (2006.01)
*A61F 2/00* (2006.01)

(52) U.S. Cl.
CPC ...... *A61F 2/0063* (2013.01); *A61F 2210/0076* (2013.01); *A61F 2250/0018* (2013.01);
(Continued)

(58) Field of Classification Search
CPC ............ A61F 2/0063; A61F 2210/0076; A61F 2250/0039;A61F 2250/0018; A61F 2250/0051
See application file for complete search history.

(56) References Cited

U.S. PATENT DOCUMENTS 5,879,336 A   3/1999 Brinon
5,879,366 A   3/1999 Shaw et al.
(Continued)

FOREIGN PATENT DOCUMENTS

JP  2005-514156 A   5/2005
JP  2005-534404 A   11/2005
(Continued)

OTHER PUBLICATIONS

Chinese Office Action issued Sep. 28, 2015 in corresponding Chinese Patent Application No. CN 2012800483129.
(Continued)

*Primary Examiner* — Ashley Fishback (57) ABSTRACT

An implantable prosthesis for repairing or reinforcing a tissue or muscle wall defect is provided. The implantable prosthesis includes a first biocompatible structure having a tether attached thereto for maintaining stable deployment of the implantable prosthesis through an abdominal wall; a rigid reinforcement member positioned adjacent a bottom side of the first biocompatible structure, the rigid reinforcement member including an inner circumferential ring, a plurality of spoke elements, a plurality of openings, and a plurality of guide members molded thereon; a mesh structure positioned adjacent a bottom surface of the rigid reinforcement member, the mesh structure overlapping the inner circumferential ring of the rigid reinforcement member; a second biocompatible structure and an anti-adhesion barrier having a collagen coating positioned on a bottom surface of the second biocompatible structure.

19 Claims, 6 Drawing Sheets

(52) U.S. Cl.
CPC ............. *A61F 2250/0039* (2013.01); *A61F 2250/0051* (2013.01)

(56) References Cited

U.S. PATENT DOCUMENTS

| | | |
|---|---|---|
| 2003/0130745 A1 | 7/2003 | Cherok et al. |
| 2006/0030881 A1 | 2/2006 | Sharkey et al. |
| 2009/0082792 A1 | 3/2009 | Koyfman et al. |
| 2010/0016872 A1 | 1/2010 | Bayon et al. |

FOREIGN PATENT DOCUMENTS

| | | |
|---|---|---|
| JP | 2010-508121 A | 3/2010 |
| JP | 2011-167538 A | 9/2011 |
| WO | 2004/012627 A1 | 5/2003 |
| WO | 2004012627 A1 | 2/2004 |
| WO | 2004019826 A1 | 3/2004 |
| WO | 2010/039249 A1 | 10/2009 |
| WO | 2010039249 A1 | 4/2010 |
| WO | WO 2010/039249 A1 | 4/2010 |

OTHER PUBLICATIONS

International Search Report for PCT/US12/58248 date of completion is Nov. 29, 2012 (one page).
Chinese Office Action issued Apr. 20, 2016 in corresponding Chinese Patent Application No. CN 201280048312.9, together with English translation, 23 pages.
Australian Office Action issued Apr. 19, 2016 in corresponding Australian Patent Application No. 2012315507, 3 pages.
Japanese Office Action mailed Jun. 24, 2016 in corresponding Japanese Patent Application No. 2014-533467, together with English translation, 7 pages.
Chinese Office Action issued Oct. 17, 2016 in corresponding Chinese Patent Application No. 201280048312.9 with English translation, 20 pages.

IMPLANTABLE PROSTHESIS FOR REPAIRING OR REINFORCING AN ANATOMICAL DEFECT

CROSS-REFERENCE TO RELATED APPLICATIONS

This application is a National Stage Application of PCT/US12/58248 under 35USC §371 (a), which claims priority of U.S. Provisional Patent Application Ser. No. 61/541,551 filed Sep. 30, 2011, the disclosures of each of the above-identified applications are hereby incorporated by reference in their entirety.

BACKGROUND

Technical Field

The present disclosure relates to implantable prostheses. More particularly, the present disclosure relates to an implantable prosthesis for repairing and/or reinforcing an anatomical defect.

Background of Related Art

In the past, in developing spaces and potential spaces within a body, blunt dissectors or soft-tipped dissectors have been utilized to create a dissected space which is parallel to the plane in which the dissectors are introduced into the body tissue. This often may be in an undesired plane, which can lead to bleeding which may obscure the field and make it difficult to identify the body structures.

In utilizing such apparatus and methods, attempts have been made to develop anatomic spaces in the anterior, posterior or lateral to the peritoneum. The same is true for plural spaces and other anatomic spaces. Procedures that have been performed in such spaces include varocele dissection, lymph node dissection, sympathectomy and hernia repair. In the past, the inguinal hernia repair has principally been accomplished by the use of an open procedure which involves an incision in the groin to expose the defect in the inguinal floor, remove the hernial sac and subsequently suture the ligaments and fascias together to reinforce the weakness in the abdominal wall.

Recently, laparoscopic hernia repairs have been attempted by inserting laparoscopic instruments into the abdominal cavity through the peritoneum and then placing a mesh to cover the hernia defect. Hernia repair using this procedure has a number of disadvantages, principally because the patch used for hernia repair is in direct contact with the structures in the abdominal cavity, as for example the intestines, so that there is a tendency for adhesions to form in between these structures. Such a procedure is also undesirable because typically the patch is stapled into the peritoneum, which is a very thin unstable layer covering the inner abdomen. Thus, the stapled patch can tear away from the peritoneum or shift its position. Other laparoscopic approaches involve cutting away the peritoneum and stapling it closed. This is time consuming and involves the risk of inadvertent cutting of important anatomic structures.

Accordingly, it is an object of the present disclosure to provide improved implantable prostheses for repairing and/or reinforcing soft tissue or muscle wall defects.

SUMMARY

Accordingly, an implantable prosthesis is provided. The implantable prosthesis includes a first biocompatible structure, a rigid reinforcement member positioned adjacent a bottom side of the first biocompatible structure, a mesh structure positioned adjacent a bottom surface of the rigid reinforcement member, a second biocompatible structure and an anti-adhesion barrier positioned on a bottom surface of the second biocompatible structure.

The first biocompatible structure includes at least one tether attached thereto. The tether may be a suture-strand tether adapted to stabilize and lift the prosthesis against an abdominal wall during surgery. Additionally, the first biocompatible structure may be configured to receive at least one peripheral fixation. The at least one peripheral fixation includes at least one or more of a tack, a suture, and a staple.

The rigid reinforcement member may be constructed from an absorbable polymer material. The rigid reinforcement member may also be configured to have a plurality of openings extending therethrough. The rigid reinforcement member further includes an inner circumferential ring and a plurality of spoke elements extending thereon. The rigid reinforcement member may further include a plurality of guide members molded thereon. The rigid reinforcement member is adapted to be partially flexible and collapsible.

In one embodiment, a stiffness of the rigid reinforcement member is greater than a stiffness of the first and second biocompatible structures.

In yet another embodiment, a diameter of the second biocompatible structure is greater than a diameter of the first biocompatible structure.

The mesh structure overlaps an inner circumferential ring of the rigid reinforcement member. The mesh structure may be constructed to promote tissue ingrowth.

In another embodiment, the anti-adhesion barrier may include a collagen coating.

In yet another embodiment, an implantable prosthesis is provided. The implantable prosthesis includes a first biocompatible structure having a tether attached thereto for maintaining stable deployment of the implantable prosthesis through an abdominal wall; a rigid reinforcement member positioned adjacent a bottom side of the first biocompatible structure, the rigid reinforcement member including an inner circumferential ring, a plurality of spoke elements, a plurality of openings, and a plurality of guide members molded thereon; a mesh structure positioned adjacent a bottom surface of the rigid reinforcement member, the mesh structure overlapping the inner circumferential ring of the rigid reinforcement member; a second biocompatible structure and an anti-adhesion barrier having a collagen coating positioned on a bottom surface of the second biocompatible structure.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Embodiments of the presently disclosed apparatus will now be described in detail with reference to the drawings, in which like reference numerals designate identical or corresponding elements in each of the several views. As used herein, the term "distal" refers to that portion of the tool, or component thereof which is further from the user while the term "proximal" refers to that portion of the tool or component thereof which is closer to the user.

While the use of the implantable prosthesis is often described herein as engaging an incision, it should be recognized that this is merely exemplary and is not intended to limit the use of the assembly in any way, but rather it should be recognized that the present disclosure is intended to be useable in all instances in situations in which the implantable prosthesis engages an incision, a naturally occurring orifice, or any other suitable opening.

Before explaining the present disclosure in detail, it should be noted that the present disclosure is not limited in its application or use to the details of construction and arrangement of parts illustrated in the accompanying drawings and description. The illustrative embodiments of the present disclosure may be implemented or incorporated in other embodiments, variations and modifications, and may be practiced or carried out in various ways. For example, although the present disclosure is described in detail as it relates to implantable prostheses for repairing umbilical hernias, it is to be understood that such devices may readily be used for repairing various other soft tissue or muscle wall defects, including but not limited to trocar site punctures, small ventral hernias etc.

However, for sake of clarity, the present disclosure will be described relating to an implantable prosthesis for repairing an anatomical defect, such as a tissue or muscle wall hernia, including an umbilical hernia, and for preventing the occurrence of a hernia at a small opening or weakness in a tissue or muscle wall, such as at a puncture tract opening remaining after completion of a laparoscopic procedure.

Surgical meshes of the present disclosure may also include at least one bioactive agent. The term "bioactive agent", as used herein, is used in its broadest sense and includes any substance or mixture of substances that have clinical use. A bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. For example, a surgical mesh may be coated with an anti-adhesive to inhibit adhesion of the mesh to tissue and/or with a local anesthetic for temporary pain relief during implantation. It is envisioned that the bioactive agent may be applied to the surgical mesh in any suitable form of matter, e.g., films, powders, liquids, gels, combinations thereof, and the like.

Figure 1:
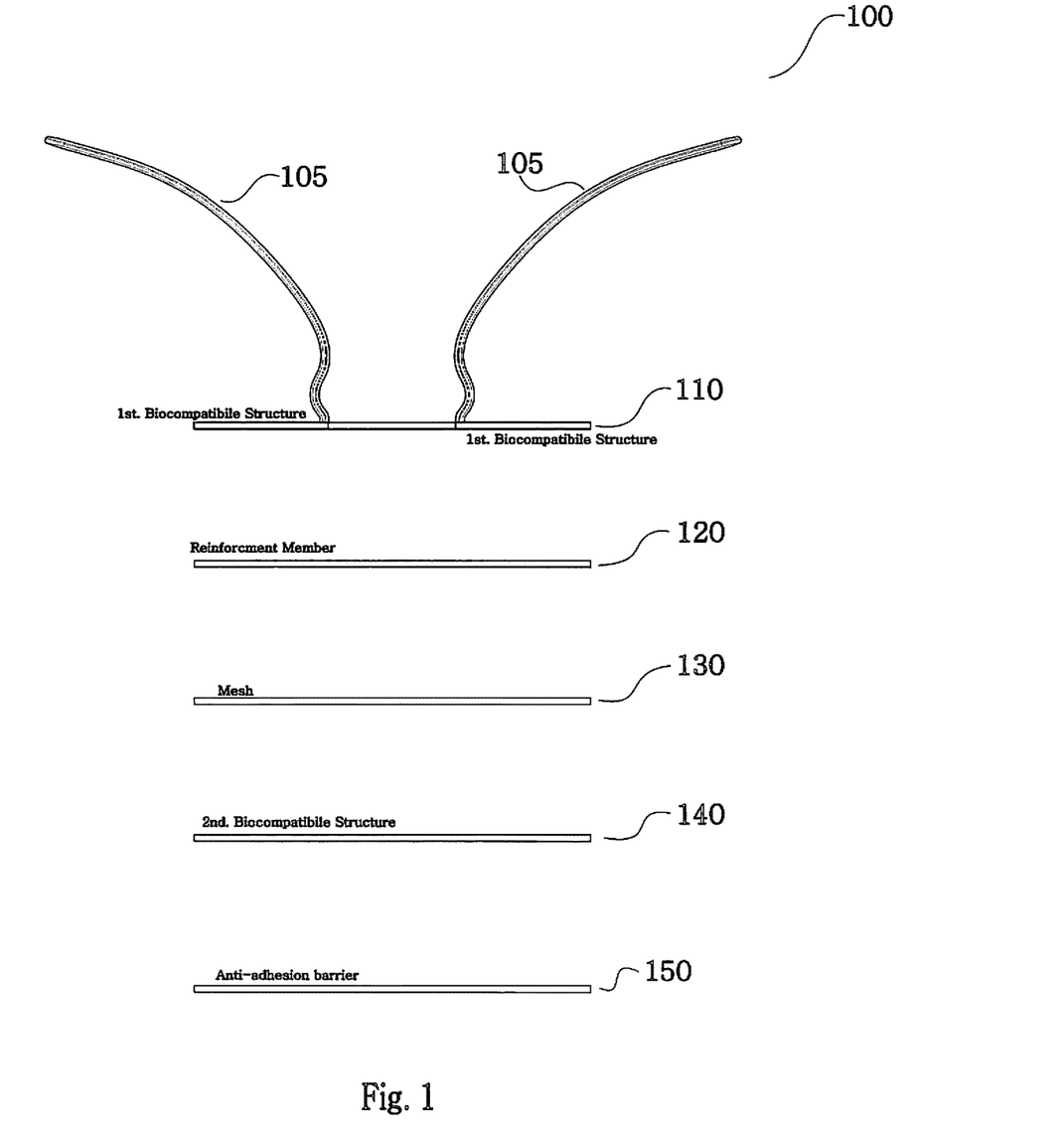
FIG. 1 is a high level diagram of the layers of an implantable prosthesis, in accordance with the present disclosure.

Referring initially to FIG. 1, layers of an implantable prosthesis are shown generally as implantable prosthesis 100. Thus, implantable prosthesis 100 is a composite prosthesis constructed from multiple elements as shown in FIGS. 1-4.

In FIG. 1, the implantable prosthesis 100 includes tethers 105 positioned on a first biocompatible structure 110. The first biocompatible structure 110 is positioned on a reinforcement member 120 positioned on a mesh structure 130. The mesh structure 130 is positioned on a second biocompatible structure 140, which in turn is positioned on an anti-adhesion barrier 150. In the illustrated embodiments, the first biocompatible structure 110, the reinforcement member 120, the mesh structure 130, the second biocompatible structure 140, and the anti-adhesion barrier 150 are substantially circular in overall shape, which is suitable for repair of typical umbilical hernia defects. Other shapes contemplated may include, but are not limited to, oval, square, rectangular, and irregular shapes.

Figure 2:
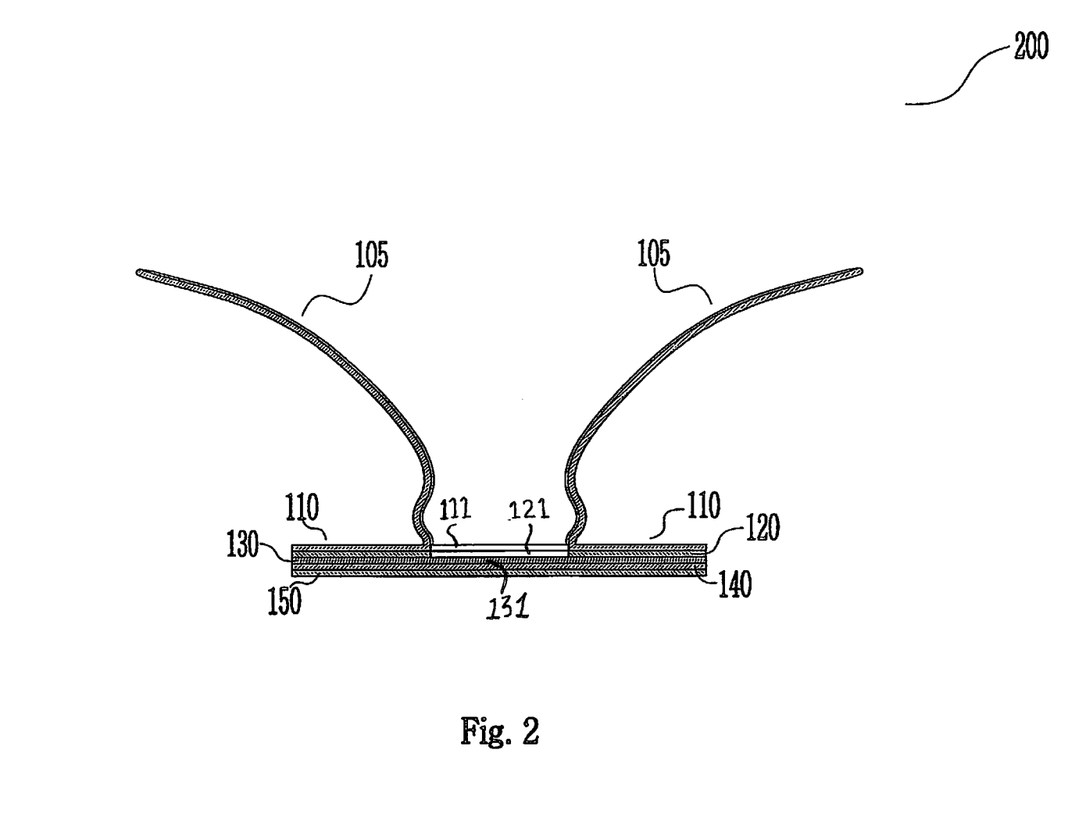
FIG. 2 is a cross sectional view of the implantable prosthesis, in accordance with the present disclosure.

In one exemplary embodiment, the biocompatible structure 110 is approximately a few millimeters to a few inches thick and the second biocompatible structure 140 is approximately a few millimeters to a few inches thick (see cross-sectional view 200 of FIG. 2). The components 105, 110, 120, 130, 140, 150 are aligned as shown in FIGS. 1, 2, and 4, and then secured together in any suitable manner, such as via bonding by heating the assembly to a desired temperature, to form the implantable prosthesis 100.

Figure 4:
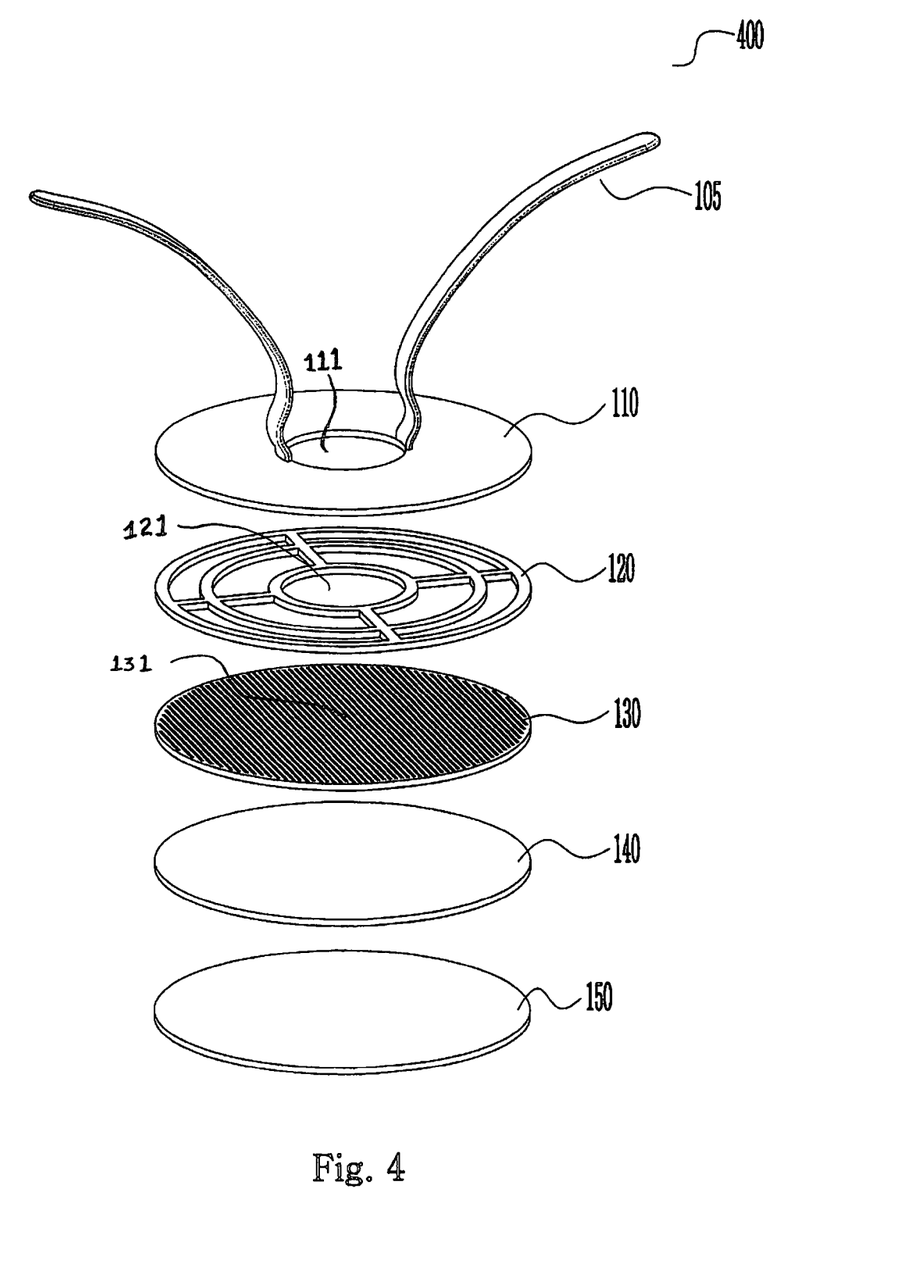
FIG. 4 is an exploded view of the layers of the implantable prosthesis, in accordance with the present disclosure.

In embodiments, as illustrated in FIGS. 2 and 4, biocompatible substrate 110 may include a first central opening 111 and reinforcement member 120 may include a second central opening 121. In embodiments, as further depicted in FIGS. 2 and 4, first central opening 111 of first biocompatible substrate 110 may be aligned (in a vertical direction) with second central opening 121 of reinforcement member 120 thereby leaving central portion 131 of mesh 130 uncovered from first biocompatible substrate 110 and reinforcement member 120.

The implantable prosthesis 100 includes at least one tether 105 that extends from the first biocompatible structure 110 and may be manipulated by a surgeon to position the implantable prosthesis 100 relative to the repair site and/or to secure the implantable prosthesis 100 relative to the opening or weakness in the tissue or muscle wall (see FIGS. 5A-8). The tether 105 may be configured to extend through the defect and outside a patient's body to allow a surgeon to position and/or manipulate the implantable prosthesis 100 from a location outside the body. A portion of the tether 105 may be attached directly to anatomy surrounding the edges of the defect opening or to other neighboring tissue, muscle, skin or other anatomy, using a suture, staple, tack or other attachment device whether separate from or integrally formed with the tether 105, so as to anchor the implantable prosthesis 100 in place. Any excess tether 105 may then be removed.

An indicator (not shown) may be arranged on the tether 105 to aid a surgeon in determining when the implantable prosthesis 100 has been inserted a sufficient depth or distance within a patient. The indicator may be located a desired distance from the implantable prosthesis 100 such that its location relative to a reference location provides an indication as to the position of the implantable prosthesis 100 within the patient without direct visualization of the implantable prosthesis 100. The tether 105 may have any suitable width, and its width may vary along the length of the tether 105. Multiple tethers 105 may be joined to the implantable prosthesis 100 to enhance the positioning and anchoring of the implantable prosthesis 100.

The first biocompatible structure 110 may be configured to receive at least one peripheral fixation. Such peripheral fixation may be at least one of a tack, suture or staple.

The reinforcement member 120 has a substantially similar size and shape as the mesh structure 130 (discussed below) and is aligned adjacent a bottom surface of the first biocompatible structure 110 (see exploded view 400 of FIG. 4). The reinforcement member 120 serves to reinforce the implant, and maintain it in a substantially flat orientation covering the defect within the patient's body. The reinforcement member 120 is substantially rigid, yet flexible enough to allow it to be collapsed for passage through the incision and defect, but resilient enough to resume the substantially flat configuration once properly placed (see FIGS. 5A-8). The reinforcement member 120 may control, in part or in whole, the direction of strain when subjected to a radial compressive force. The reinforcement member 120 described herein has been found particularly suitable for these purposes, and its configuration greatly improves resistance to collapsing or buckling of the implant after placement. The disclosed configuration provides the additional benefit of controlling the direction of strain of the implant during placement.

The reinforcement member 120 contributes to the stability of the mesh structure 130, thus allowing it to deploy into and remain in a desired shape. For example, the reinforcement member 120 may aid in returning the mesh structure 130 to a substantially unfurled or expanded configuration after the folded up or otherwise reduced implant has been delivered through the cannula (see FIGS. 5A-8). This stability facilitates deployment and placement of the reinforcement member 120 by making it easy to handle. Also, this stability minimizes the tendency of the reinforcement member 120 to sag, fold, bend, collapse, or otherwise be dislocated. Difficulty in handling, dislocation or bending may require additional operative procedures and/or additional anchoring during implantation.

Figure 3:
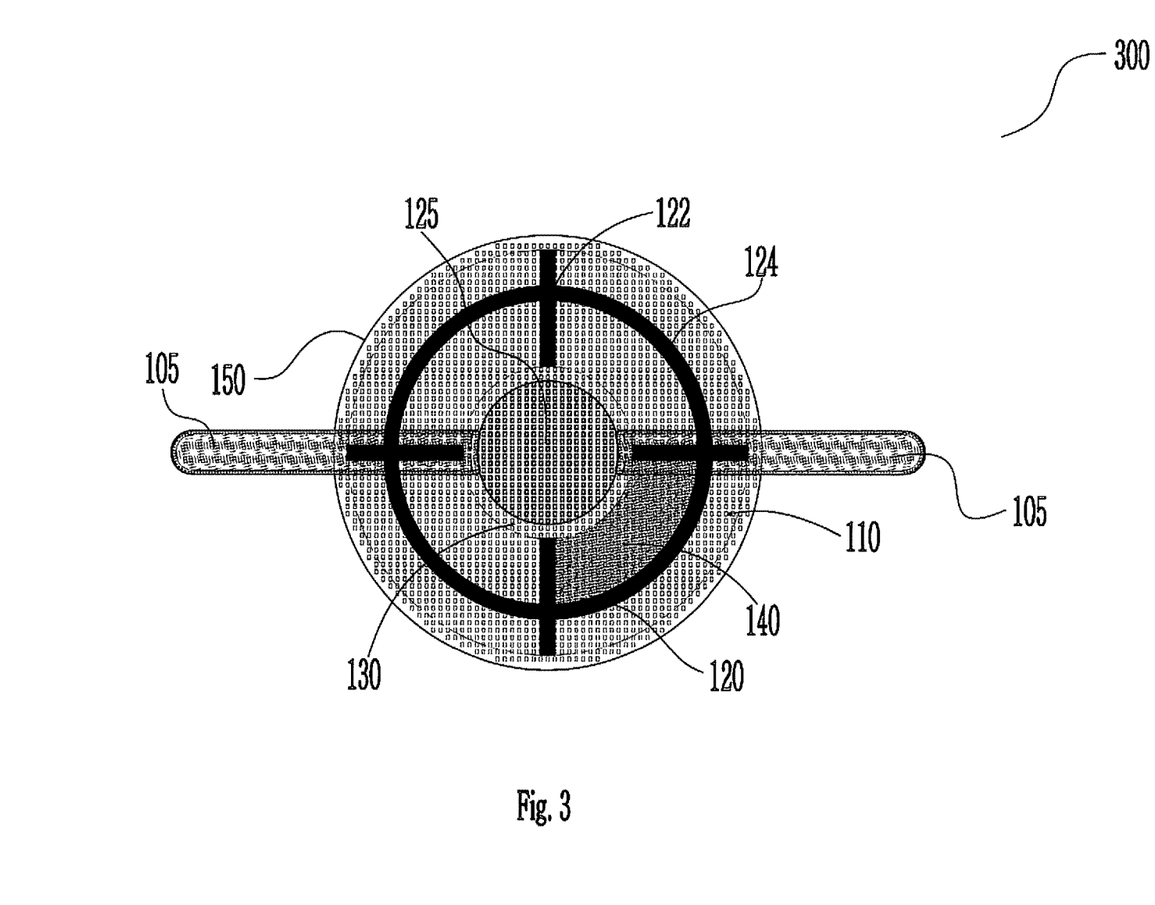
FIG. 3 is a top view of the implantable prosthesis, in accordance with the present disclosure.

While the exemplary embodiments illustrate a semi-toroidal shape, it should be noted that any symmetrical dimensional form, such as a spherical shape, would provide the same functional benefit during installation. As shown in FIGS. 1, 3 and 4, the reinforcement member 120 has a somewhat toroidal shape, with an optional outer circumferential ring lying substantially in a first horizontal plane and an inner circumferential ring 124 lying substantially in a second horizontal plane (see top view 300 of FIG. 3). Spoke like elements 122 may extend therebetween. The reinforcement member 120 may be made of, for example, an absorbable material, such as polydioxanone, with a thickness of approximately a few millimeters to a few inches, which renders its stiffness greater than that of the first or second biocompatible structures 110, 140.

In another exemplary embodiment, the reinforcement member 120 may further include one or more rib-like elements (not shown) extending longitudinally along portions of the spoke-like elements 122. The rib elements may further reinforce and provide stability to the implant and prevent permanent inversion of the formed shape from transient compression perpendicular to the plane of the center portion of the reinforcement member 120.

In another exemplary embodiment, the reinforcement member 120 may further include a plurality of guide members (not shown) molded thereon. The plurality of guide members may aid in the positioning of needles or surgical instruments. Also, the stiffness of the reinforcement member 120 may be greater than the stiffness of the first and second biocompatible structures 110, 140.

The mesh structure 130 may be configured to have any suitable shape or size that is conducive to facilitating the correction or repair of a particular defect. The mesh structure 130 described herein has been found particularly suitable for these purposes, and the illustrated configuration greatly improves resistance to collapsing or buckling of the implant after placement. The illustrated configuration provides the additional benefit of controlling the direction of strain of the implant during placement.

In the exemplary embodiment shown in FIGS. 1-4, the mesh structure 130 has a relatively flat configuration. However, the mesh structure 130 need not be flat, and convex, concave, convex/concave, and more complex shapes also are contemplated. The mesh structure 130 may be pliable to facilitate manipulation and/or reduction of the implantable prosthesis 100 during delivery to the defect and/or to conform the implantable prosthesis 100 to the anatomical site of interest. As illustrated in FIGS. 1-4, the mesh structure 130 has a generally circular shape. Examples of other shapes include, but are not limited to, oval, square, rectangular, and irregular configurations.

Additionally, the mesh structure 130 may include one or more layers of repair fabric that may promote tissue ingrowth to the mesh structure 130, inhibit adhesions to the mesh structure 130, or a combination of both. In one illustrative embodiment, the mesh structure 130 includes an ingrowth layer (not shown) having a plurality of interstices or openings which allow sufficient tissue or muscle ingrowth to integrate the prosthesis with the host tissue or muscle after implantation.

Moreover, the anti-adhesion barrier 150 provides a bioresorbable layer that physically separates and protects the non-absorbable polypropylene mesh structure 130 and/or implantable prosthesis 100 from underlying tissue and organ surfaces during the wound-healing period to minimize tissue attachment to the polypropylene mesh. The anti-adhesion barrier 150 may also include a collagen coating.

In the exemplary embodiments, biocompatible structures 110, 140 may be constructed from, at least one of a biodegradable polyglycolic acid, a swine submucosal intestine, a collagen, or a polylactic acid. Other suitable suturing (and band) materials include, e.g., polymeric materials such as polyethylene teraphthalate (PET), polyester (e.g., Dacron™), polypropylene, polyethylene, polycarbonate urethane or metallic material include, e.g., titanium, nickel titanium alloy, stainless steel, surgical steels or any combinations thereof.

With reference to FIGS. 5A-8, the operation of the implantable prosthesis 100 is described.

In use, the implantable prosthesis 100 may be placed at the defect site using an open surgical procedure, by laparoscopically passing the implantable prosthesis 100 through a cannula (not shown) that extends along a puncture tract leading to the defect, such as may be formed naturally or by a trocar, or through a hybrid procedure where an incision is formed through the skin and then a tract is created in the underlying tissue and/or muscle leading to the defect site along which the repair device is transported. The implantable prosthesis 100 may be flexible, allowing reduction of the implantable prosthesis 100, such as by folding, rolling or otherwise collapsing implantable prosthesis 100, into a slender configuration suitable for delivery along the puncture tract, or a cannula extending through the puncture tract, to the defect site. Upon exiting the puncture tract or cannula, the implantable prosthesis 100 may automatically unfurl or may be unfolded, unrolled or otherwise deployed by the surgeon to an unfurled or expanded configuration suitable to repair the weakness or opening.

Figure 5A:
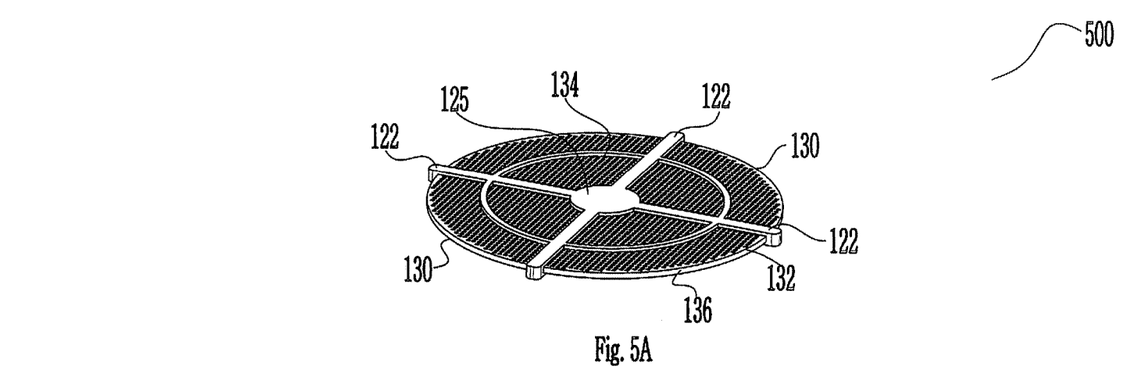
FIGS. 5A-5C illustrate an implantable prosthesis for FIGS. 1-4, and collapsed views thereof, in accordance with the present disclosure.
Figure 5B:
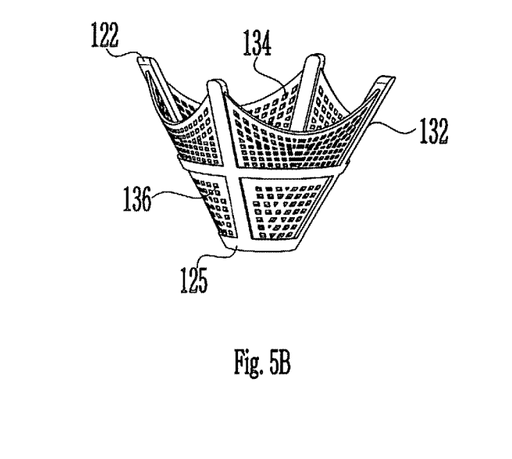
Figure 5C:
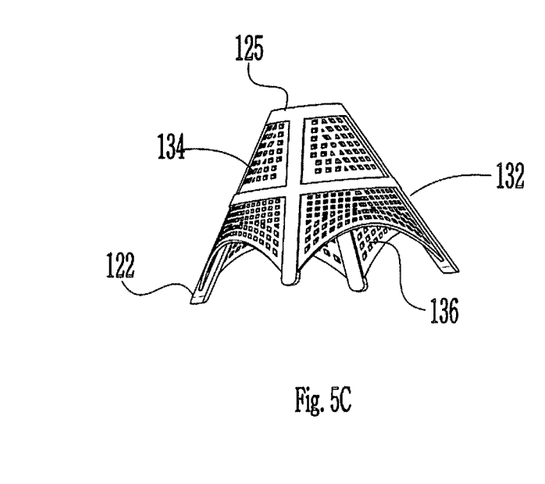
Figure 6:
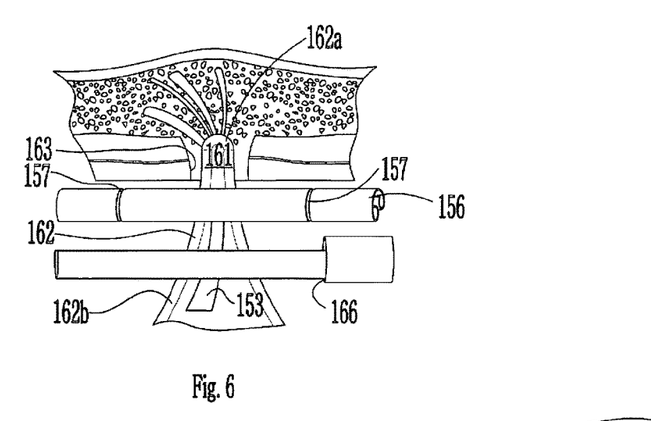
FIG. 6 is a sagittal view showing the attachment of a mesh structure to a hernia sac, in accordance with the present disclosure.
Figure 7:
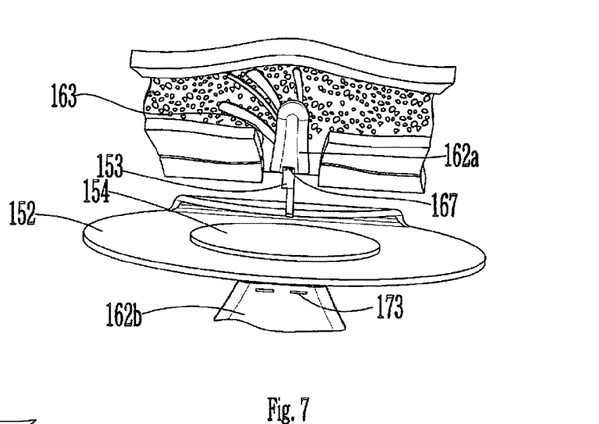
FIG. 7 is a sagittal view similar to FIG. 6 showing the dissection of the hernia sac and the unrolling of the mesh structure, in accordance with the present disclosure.
Figure 8:
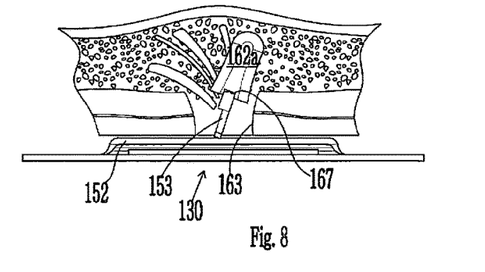
FIG. 8 is a sagittal view showing the mesh structure in place to provide the hernia repair, in accordance with the present disclosure.

In exemplary embodiment 500, as shown in FIGS. 5A-5C, the implantable prosthesis 100 is substantially umbrella shaped, having a central hub 125 with radially extending spokes 122. Each of the spokes 122 may be joined to the adjacent spokes 122 by a mesh structure 130, forming a radial extension 132 about the central hub 125. The radial extension 132 has an upper surface 134 and a lower surface 136, where the upper surface 134 contours to the shape of the inner wall when inserted as shown in FIGS. 6-8, and where the lower surface 136 contours to the shape of the inner wall when inserted as shown in FIGS. 6-8. The radial extension 132 may be substantially circular, elliptical, or rectangular in plan shape. The spokes 122 are formed from flexible material, allowing the radial extension 132 to be collapsed for insertion into an aperture, and then expand conforming to the shape of the inner wall of the cavity (see FIGS. 6-8). In the collapsed position, the implantable prosthesis 100 may be substantially frustoconical or shuttlecock shaped.

In an alternative embodiment, the radial extension 132 has a greater thickness at the central hub 125 edge than at the outside edge.

Referring to FIGS. 6-8, laparoscopic instruments (not shown) may be utilized which are introduced through cannulas (not shown) while visualizing the same through, for example, a laparoscope introduced through an introducer device to dissect the hernia 161 to permit visualization of its neck 162 as it is entering the internal inguinal ring 163.

In use, the roll 156, after it is in the preperitoneal space, is manipulated so that its tail 153 is disposed alongside the neck 162 of the hernia sac 161 as shown in FIGS. 6-8. A stapling device 166 (see FIG. 6) is then introduced through the cannula to staple the tail 153 to the neck 162 by placing staples 167 therein (see FIGS. 7 and 8). These staples 167 serve to divide the neck of the hernia sac 161 into distal and proximal portions 162a and 162b. As soon as this stapling operation is completed, the two portions 162a and 162b are separated from each other because of the pressure of the insufflation gas causes the tail 153 of the mesh structure 130 (see FIGS. 7 and 8) to be pulled upwardly into the inguinal ring to pull with it the prosthesis 300 (see FIG. 8). The sutures 157 are cut apart to permit the prosthesis 300 to unroll and to be placed across the inguinal ring 163 (see FIGS. 6 and 8), which created the main weakness in the abdominal wall permitting the hernia which is being repaired to occur. The proximal portion 162b of the neck 162 is stapled together by staples 173 as shown in FIG. 7. The proximal portion 162 is then permitted to fold back into the desired anatomical location within the abdomen.

A tail 153 may be secured to the prosthesis 300 substantially in the center thereof, in a suitable manner. For example, as shown, the tail 153 may be provided with split portions, which are split apart and offset with respect to each other, which are secured to an inner circumferential ring 124 of the reinforcement member 120 (see FIG. 7) and secured to the first biocompatible structure 110 by suitable means. The tail 153 may be formed of the same material as the first biocompatible structure 110, or it can be formed of a different material, such as Goretex®.

As such, in accordance with FIGS. 6-8, anatomic spaces may be created in various parts of the human body, for example in the preperitoneal area to provide a space anterior to the peritoneum for hernia repair and for varocele dissection. Additionally, the mesh structure 130, as well as the reinforcement member 120 of the implantable prosthesis 100 aid in the creation of a stable, rigid structure appropriate for performing laparoscopic hernia repair.

It is understood that there may be a variety of device designs of mesh structures 130 or reinforcement members 120 or biocompatible structures 110, 140 to accomplish the expansion of a device from a first configuration, to a second configuration to occupy at least a portion of the sub-annular space and reduce re-extrusion of the nucleus. These devices may be constructed of single components or multiple components, with a variety of different materials, whether synthetic, naturally occurring, recombinated (genetically engineered) to achieve various objectives in the repairing and/or reinforcing of soft tissue or muscle wall defects.

Moreover, meshes structures 130, reinforcement members 120, and/or biocompatible structures 110, 140 may be attached in a number of methods. It should be appreciated that the present disclosure is not limited to any particular attachment method. For example, the layers (see FIG. 1) may be bonded together by melting the layers at specific locations or in a specific pattern; sonic, induction, vibration, or infrared/laser welding the layers; or using a suitable bonding agent. The point or points of attachment may comprise any suitable pattern, such as a spiral pattern, a serpentine pattern, or a grid-like pattern of dots or beads, that maintains a sufficient quantity of open or non-impregnated interstices for tissue or muscle infiltration.

Implantable prostheses of the present disclosure include a first biocompatible structure, a rigid reinforcement member positioned adjacent a bottom side of the first biocompatible structure, a mesh structure positioned adjacent a bottom surface of the rigid reinforcement member, a second biocompatible structure, and an anti-adhesion barrier positioned on a bottom surface of the second biocompatible structure.

In any of the presently disclosed embodiments, the first biocompatible structure includes at least one tether attached thereto. In any of the presently disclosed embodiments, the tether is a suture-strand tether adapted to stabilize and lift the prosthesis against an abdominal wall during surgery. In any of the presently disclosed embodiments, the first biocompatible structure is configured to receive at least one peripheral fixation. In any of the presently disclosed embodiments, the at least one peripheral fixation includes at least one or more of a tack, a suture, and a staple. In any of the presently disclosed embodiments, the rigid reinforcement member is constructed from an absorbable polymer material. In any of the presently disclosed embodiments, the rigid reinforcement member is configured to have a plurality of openings extending therethrough. In any of the presently disclosed embodiments, the rigid reinforcement member includes an inner circumferential ring and a plurality of spoke elements extending thereon. In any of the presently disclosed embodiments, the rigid reinforcement member includes a plurality of guide members molded thereon. In any of the presently disclosed embodiments, the rigid reinforcement member is adapted to be partially flexible and collapsible. In any of the presently disclosed embodiments, a stiffness of the rigid reinforcement member is greater than a stiffness of the first and second biocompatible structures. In any of the presently disclosed embodiments, a diameter of the second biocompatible structure is greater than a diameter of the first biocompatible structure. In any of the presently disclosed embodiments, the mesh structure overlaps an inner circumferential ring of the rigid reinforcement member. In any of the presently disclosed embodiments, the mesh structure promotes tissue ingrowth. In any of the presently disclosed embodiments, the anti-adhesion barrier includes a collagen coating. In any of the presently disclosed embodiments, the prosthesis is used as an open umbilical hernia repair device.

Additionally, the presently disclosed implantable prosthesis includes a first biocompatible structure having a tether attached thereto for maintaining stable deployment of the implantable prosthesis through an abdominal wall, a rigid reinforcement member positioned adjacent a bottom side of the first biocompatible structure, the rigid reinforcement member including an inner circumferential ring, a plurality of spoke elements, a plurality of openings, and a plurality of guide members molded thereon, a mesh structure positioned adjacent a bottom surface of the rigid reinforcement member, the mesh structure overlapping the inner circumferential ring of the rigid reinforcement member, a second biocompatible structure, and an anti-adhesion barrier having a collagen coating positioned on a bottom surface of the second biocompatible structure.

In any of the presently disclosed embodiments, the mesh structure is configured to promote tissue ingrowth. In any of the presently disclosed embodiments, a stiffness of the rigid reinforcement member is greater than a stiffness of the first and second biocompatible structures.

Additionally, the description and illustrations described previously may be directed and illustrative of various spinal applications of the present disclosure, it is possible that the inventive methods, devices and delivery tools may be applied to the repair, fixation, augmentation, reinforcement, support or otherwise generally prophylactically or therapeutically treating other tissues.

Moreover, the drawings and descriptions herein are necessarily simplified to depict the operation of the devices and illustrate various steps in the method. In use, the tissues may be manipulated by, and are frequently in contact with, the various tools and devices; however, for clarity of construction and operation, the figures may not show intimate contact between the tissues the tools and the devices.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. As well, one skilled in the art will appreciate further features and advantages of the present disclosure based on the above-described embodiments. Accordingly, the present disclosure is not to be limited by what has been particularly shown and described, except as indicated by the appended claims.

The invention claimed is:

1. An implantable prosthesis comprising:
a first biocompatible structure including at least one tether attached thereto and extending therefrom to allow manipulation of the implantable prosthesis from outside a patient's body;
a rigid reinforcement member positioned adjacent a bottom side of the first biocompatible structure;
a mesh structure positioned adjacent a bottom surface of the rigid reinforcement member;
a second biocompatible structure; and
an anti-adhesion barrier positioned on a bottom surface of the second biocompatible structure.

2. The implantable prosthesis according to claim 1, wherein the first biocompatible structure further comprises a first central opening and the rigid reinforcement member further comprises a second central opening, wherein the first and second central openings are aligned and a central portion of the mesh structure is uncovered.

3. The implantable prosthesis according to claim 1, wherein the at least one tether is a suture-strand tether adapted to stabilize and lift the prosthesis against an abdominal wall during surgery.

4. The implantable prosthesis according to claim 1, wherein the first biocompatible structure is configured to receive at least one peripheral fixation.

5. The implantable prosthesis according to claim 4, wherein the at least one peripheral fixation includes at least one or more of a tack, a suture, and a staple.

6. The implantable prosthesis according to claim 1, wherein the rigid reinforcement member is constructed from an absorbable polymer material.

7. The implantable prosthesis according to claim 1, wherein the rigid reinforcement member includes a plurality of openings extending therethrough.

8. The implantable prosthesis according to claim 1, wherein the rigid reinforcement member includes an inner circumferential ring and a plurality of spoke elements extending thereon.

9. The implantable prosthesis according to claim 1, wherein the rigid reinforcement member includes a plurality of guide members molded thereon.

10. The implantable prosthesis according to claim 1, wherein the rigid reinforcement member is adapted to be partially flexible and collapsible.

11. The implantable prosthesis according to claim 1, wherein a stiffness of the rigid reinforcement member is greater than a stiffness of the first and second biocompatible structures.

12. The implantable prosthesis according to claim 1, wherein a diameter of the second biocompatible structure is greater than a diameter of the first biocompatible structure.

13. The implantable prosthesis according to claim 1, wherein the mesh structure overlaps an inner circumferential ring of the rigid reinforcement member.

14. The implantable prosthesis according to claim 1, wherein the mesh structure promotes tissue ingrowth.

15. The implantable prosthesis according to claim 1, wherein the anti-adhesion barrier includes a collagen coating.

16. The implantable prosthesis according to claim 1, wherein the prosthesis is used as an open umbilical hernia repair device.

17. An implantable prosthesis for repairing or reinforcing a tissue or muscle wall defect, the prosthesis comprising:
a first biocompatible structure having a tether attached thereto and extending therefrom for maintaining stable deployment of the implantable prosthesis through an abdominal wall from outside a patient's body;
a rigid reinforcement member positioned adjacent a bottom side of the first biocompatible structure, the rigid reinforcement member including an inner circumferential ring, a plurality of spoke elements, a plurality of openings, and a plurality of guide members molded thereon;

a mesh structure positioned adjacent a bottom surface of the rigid reinforcement member, the mesh structure overlapping the inner circumferential ring of the rigid reinforcement member;

a second biocompatible structure; and an anti-adhesion barrier having a collagen coating positioned on a bottom surface of the second biocompatible structure.

18. The implantable prosthesis according to claim 17, wherein the mesh structure is configured to promotes tissue ingrowth.

19. The implantable prosthesis according to claim 17, wherein a stiffness of the rigid reinforcement member is greater than a stiffness of the first and second biocompatible structures.

* * * * *